(12) United States Patent
Islam

(10) Patent No.: US 7,294,105 B1
(45) Date of Patent: Nov. 13, 2007

(54) SYSTEM AND METHOD FOR A WIRELESS MEDICAL COMMUNICATION SYSTEM

(75) Inventor: Mohammed N. Islam, Ann Arbor, MI (US)

(73) Assignee: Cheetah Omni, LLC, Ann Arbor, MI (US)

( * ) Notice: Subject to any disclaimer, the term of this patent is extended or adjusted under 35 U.S.C. 154(b) by 150 days.

(21) Appl. No.: 10/652,275

(22) Filed: Aug. 29, 2003

Related U.S. Application Data (60) Provisional application No. 60/408,028, filed on Sep. 3, 2002.

(51) Int. Cl.
*A61B 5/00* (2006.01)

(52) U.S. Cl. .................. 600/300; 128/903; 128/904

(58) Field of Classification Search ........ 600/300–301; 128/903–905, 920
See application file for complete search history.

(56) References Cited

U.S. PATENT DOCUMENTS

| | | | | |
|---|---|---|---|---|
| 5,458,122 | A | 10/1995 | Hethuin | 128/696 |
| 5,617,871 | A | 4/1997 | Burrows | 128/696 |
| 5,687,734 | A | 11/1997 | Dempsey et al. | 128/696 |
| 5,704,351 | A | 1/1998 | Mortara et al. | 128/630 |
| 5,718,234 | A | 2/1998 | Warden et al. | 128/696 |
| 5,748,103 | A | 5/1998 | Flach et al. | 340/870.07 |
| 5,855,550 | A | 1/1999 | Lai et al. | 600/300 |
| 5,862,803 | A | 1/1999 | Besson et al. | 128/696 |
| 5,944,659 | A | 8/1999 | Flach et al. | 600/300 |
| 5,957,854 | A | 9/1999 | Besson et al. | 600/509 |
| 6,289,238 | B1 | 9/2001 | Besson et al. | 600/509 |
| 6,364,834 | B1 | 4/2002 | Reuss et al. | 600/300 |
| 6,402,691 | B1 | 6/2002 | Peddicord et al. | 600/300 |
| 6,441,747 | B1 | 8/2002 | Khair et al. | 340/870.16 |
| 6,443,890 | B1 | 9/2002 | Schulze et al. | 600/300 |
| 6,454,705 | B1 | 9/2002 | Cosentino et al. | 600/300 |
| 6,659,947 | B1 * | 12/2003 | Carter et al. | 600/300 |
| 6,802,811 | B1 * | 10/2004 | Slepian | 600/309 |

(Continued)

FOREIGN PATENT DOCUMENTS

WO  WO 01/89362 A2  11/2001

(Continued)

OTHER PUBLICATIONS

I.B. Aris, A.A.E. Wagie, N.B. Mariun, A.B.E. Jammal, "An Internet-based blood pressure monitoring system for patients," Journal of Telemedicine and Telecare, pp. 51-53, 2001.

(Continued)

*Primary Examiner*—Max Hindenburg
*Assistant Examiner*—Michael C Astorino
(74) *Attorney, Agent, or Firm*—Baker Botts L.L.P.

(57) ABSTRACT

In one embodiment, a wireless medical communication system includes a plurality of transmitters. Each of the plurality of transmitters is capable of being coupled to at least one of a plurality of patients and operable to communicate over a communication link a substantially unprocessed physiological data signal associated with at least one patient. At least a portion of the communication link comprises a wireless connection. The system further includes at least one medical diagnostic device operable to receive at least two substantially unprocessed physiological data signals communicated from the plurality of transmitters. Each of the at least two substantially unprocessed physiological data signals are associated with different patients.

56 Claims, 6 Drawing Sheets

U.S. PATENT DOCUMENTS

| | | | |
|---|---|---|---|
| 2002/0013518 A1 | 1/2002 | West et al. | 600/300 |
| 2002/0019584 A1 | 2/2002 | Schulze et al. | 600/300 |
| 2002/0058861 A1 | 5/2002 | Drew | 600/300 |
| 2002/0109621 A1 | 8/2002 | Khair et al. | 341/174 |
| 2002/0115914 A1 | 8/2002 | Russ | 600/300 |

FOREIGN PATENT DOCUMENTS

| | | |
|---|---|---|
| WO | WO 02/27640 A2 | 4/2002 |
| WO | WO 02/28123 A2 | 4/2002 |

OTHER PUBLICATIONS

R.H. Istepanian, B. Woodward, P.A. Balos, S. Chen, B. Luk, "The comparative performance of mobile telemedical systems based on the IS-54 and GSM cellular telephone stanards," Journal of Telemedicine and Telecare, pp. 97-104, 1999.

* cited by examiner

SYSTEM AND METHOD FOR A WIRELESS MEDICAL COMMUNICATION SYSTEM

RELATED APPLICATIONS

This application claims the benefit under 35 U.S.C. §119 (e) of U.S. Provisional Patent Application No. 60/408,028 entitled "Untethered Patient with Wireless Connection Between Patient and Medical Instruments or Devices" filed Sep. 3, 2002.

TECHNICAL FIELD OF INVENTION

This invention relates generally to medical communication systems and more particularly to a system and method for a wireless medical communication system.

OVERVIEW

During the medical treatment of patients, sensors are used to monitor and record the patient's physiological parameters. In most cases, these sensors require tethering the patient to a medical diagnostic device that processes and/or analyzes the information collected. Conventional patient data collection systems tether the patient to the medical diagnostic device through the use of an "umbilical cord" having multiple wires. The use of the umbilical cord can, in some cases, restrict the mobility of the patient.

SUMMARY OF EXAMPLE EMBODIMENTS

In one embodiment, a wireless medical communication system includes a plurality of transmitters. Each of the plurality of transmitters is capable of being coupled to at least one of a plurality of patients and operable to communicate over a communication link a substantially unprocessed physiological data signal associated with at least one patient. At least a portion of the communication link comprises a wireless connection. The system further includes at least one medical diagnostic device operable to receive at least two substantially unprocessed physiological data signals communicated from the plurality of transmitters. Each of the at least two substantially unprocessed physiological data signals are associated with different patients.

In another embodiment, a wireless medical communication system capable of minimizing interference includes one or more sensors coupled to at least one patient and operable to convert at least one physiological parameter associated with the at least one patient to a substantially unprocessed physiological data signal. The system also includes at least one transmitter coupled to the one or more sensors. The at least one transmitter is operable to communicate over a communication link the substantially unprocessed physiological data signal. At least a portion of the communication link comprises a wireless connection. At least a portion of the wireless connection operates in a Wireless Medical Telemetry Service (WMTS) band.

In yet another embodiment, a method for wirelessly communicating data using a Query-Need-To-Know (QNN) protocol includes generating, at a base station, an update request comprising a query capable of being used to update one or more parameters associated with a user. The method also includes communicating the update request to the user over a communication link. At least a portion of the communication link comprises a wireless connection. The method further includes authenticating the update request at the user and, after authenticating the update request, communicating, to the base station, the one or more updated parameters associated with the user.

In still another embodiment, wireless medical communication system including at least one transmitter coupled to at least one patient. The at least one transmitter is operable to communicate over a first communication link a substantially unprocessed physiological data signal associated with the at least one patient. At least a portion of the first communication link comprises a wireless connection. The system also includes at least one central instrumentation facility coupled to the at least one transmitter and operable to process at least a portion of the substantially unprocessed physiological data signal. The system further includes at least one bed-side data station coupled to the at least one central facility and located in a patient room associated with the at least one patient. The at least one bed-side station is operable to receive the processed physiological data signal from the at least one central facility over a second communication link.

In yet another embodiment, a wireless medical communication system includes one or more sensors coupled to at least one patient and operable to convert at least one physiological parameter associated with the at least one patient to a substantially unprocessed physiological data signal. The system also includes at least one transmitter coupled to the at least one patient. The at least one transmitter is operable to communicate over a communication link the substantially unprocessed physiological data signal. At least a portion of the communication link comprises a wireless connection. At least a portion of substantially unprocessed physiological data signal is communicated using a data format capable of minimizing interference. The system further includes at least one receiver coupled to the at least one transmitter. The at least one receiver is operable to receive at least a portion of the substantially unprocessed physiological data signal.

Depending on the specific features implemented, particular embodiments may exhibit some, none, or all of the following technical advantages. Various embodiments may be capable of untethering a patient from one or more medical devices. Some embodiments may be capable of reducing the cost of a medical monitoring system by sharing medical instruments between patients. Other embodiments may provide an improved network for remote monitoring of a soldier's physiological parameters in a military environment Other technical advantages will be readily apparent to one skilled in the art from the following figures, description, and claims. Moreover, while specific advantages have been enumerated, various embodiments may include all, some, or none of the enumerated advantages.

BRIEF DESCRIPTION OF THE DRAWINGS

To provide a more complete understanding of the present invention and certain features and advantages, thereof, reference is made to the following description taken in conjunction with the accompanying drawings, in which.

DESCRIPTION OF EXAMPLE EMBODIMENTS

Figure 1:
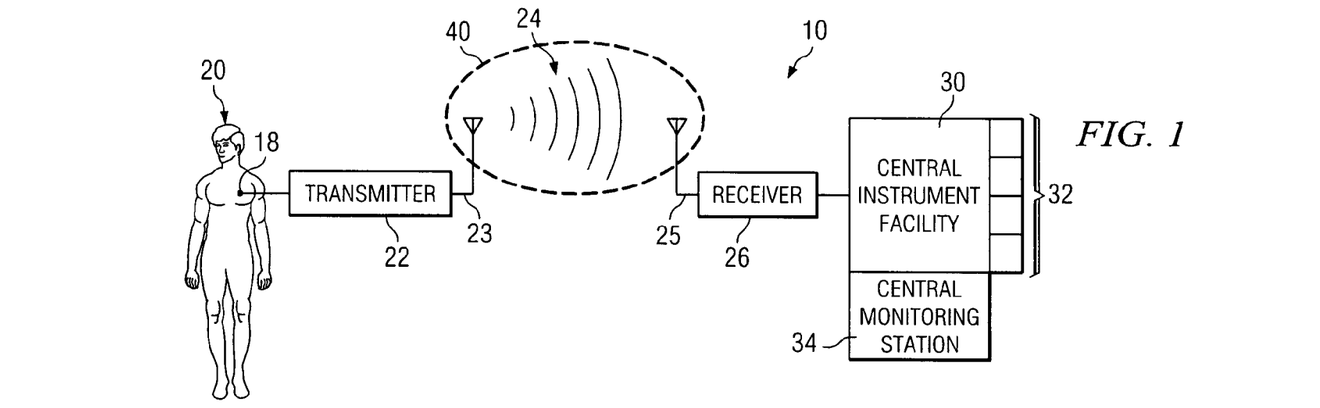
FIG. 1 is a block diagram of one embodiment of a medical communication system for communicating physiological parameters of a patient over a communication link.

FIG. 1 is a block diagram of one embodiment of a medical communication system 10 for communicating physiological parameters of a patient 20 over a communication link 40. In this embodiment, system 10 includes a sensor 18, a transmitter 22, a receiver 26, and a central instrument facility (CIF) 30. In this example, system 10 also includes medical diagnostic devices 32 and central monitoring station (CMS) 34. In various embodiments, system 10 may be capable of collecting, processing, and/or monitoring physiological information associated with patient 20.

In this embodiment, sensor 18 is coupled to the body of patient 20. As used throughout this document, the term "couple" and or "coupled" refers to any direct or indirect communication between two or more elements, whether or not those elements are in physical contact with one another. Although, in this example, sensor 18 comprises a single sensor, any additional number of sensors may be used without departing from the scope of the present disclosure. For example, patient 20 may be coupled to several sensors each capable of monitoring one or more physiological parameters of patient 20.

In various embodiments, sensor 18 may comprise a semiconductor-based device, such as an Ion Sensitive Field Effect Transistor (ISFET), a Metal Oxide Silicon (MOS) gas sensor, a barrier layer temperature sensor, one or more photodiodes, or a combination of these or other devices. Implementing a semiconductor-based sensor is advantageous because of their small size, sensitivity, high integration capability, and low electrical current consumption. Alternatively, sensor 18 may comprise a thin-layer technology sensor or air-humidity sensor. Although specific types of sensor 18 are described, sensor 18 may comprise any other suitable devices without departing from the scope of the present disclosure.

In this embodiment, sensor 18 comprises multiple electrodes that facilitate monitoring one or more physiological data points from one or more locations on the body of patient 20. Although sensor 18 comprises multiple electrodes in this example, any number of electrodes may be used without departing from the scope of the present disclosure. In one embodiment, sensor 18 may attach a patient and/or sensor identification code to the monitored physiological data that enables CIF 30 to associate the data with patient 20 upon receipt. Attaching an identification code to the monitored physical data can advantageously prevent system 10 from associating the data with the wrong sensor, which may result from inputting the data into the wrong port on transmitter 22.

In this example, sensor 18 operates to monitor one or more physiological parameters of patient 20 and to convert the monitored physiological parameters into an electronic format or data. The physiological parameters monitored by sensor 18 may include parameters such as oxygen saturation in the blood (SpO2), blood pressure, blood sugar, body temperature, an electrocardiogram (ECG), an electroencephalogram (EEG), respiration rate, heart rate, or a combination of these or other parameters. In some cases, complex parameters, such as ECG and EEG, may require system 10 to communicate the physiological data at a higher transmission rate to generate real-time graphs and/or pictures of the monitored parameter.

In this embodiment, transmitter 22 is coupled to sensor 18. Although transmitter 22 comprises a single transmitter in this example, any other number of transmitters may be used without departing from the scope of the present disclosure. In an alternate embodiment, transmitter 22 may be coupled to multiple sensors 18, each sensor capable of monitoring one or more physiological parameters of patient 20. Transmitter 22 may comprise any device capable of communicating physiological data signals 24 associated with patient 20 to one or more receivers 26. In some embodiments, transmitter 22 may comprise a transceiver capable of communicating and receiving signals 24 to and/or from receiver 26 or any other communication device. In some embodiments, one or more antennas 23 may be coupled to or may be contained within transmitter 22. Antenna 23 may comprise any device capable of communicating data signals 24 between transmitter 22 and receiver 26.

In this example, transmitter 22 comprises a device that is capable of being attached to patient 20. In this manner, transmitter 22 may allow patient 20 to move freely without interrupting the monitoring of the physiological data associated with patient 20. Transmitter 22 may be attached to patient 20 by, for example, coupling transmitter 22 to patient 20, by clipping transmitter 22 to a medical gown worn by patient 20, or in any other suitable manner. In some embodiments, transmitter 22 may be implanted inside the body of patient 20.

In this particular embodiment, transmitter 22 communicates data signals 24 based at least in part on wireless technology, such as cordless telephone, wireless Internet, cellular, IEEE 802.11, 802.11b, and/or WiFi technologies. Although this example implements wireless technology, any other communication technology may be used without departing from the scope of the present disclosure. In this example, data signals 24 comprises substantially unprocessed physiological data collected from patient 20. As used throughout this document, the phrase "substantially unprocessed physiological data" can include unprocessed physiological data, partially processed physiological data, the combination of unprocessed physiological data and a patient/sensor identification code, or the combination of partially processed physiological data and a patient/sensor identification code. For example, data signals 24 may comprise the unprocessed physiological data and a patient/sensor identification code generated by transmitter 22 or sensor 18. In other embodiments, data signals 24 may comprise modified and/or processed signals associated with the physiological data collected from patient 20.

Most conventional medical telemetry systems currently employ the Industrial, Scientific, and Medical (ISM) communication band, which is susceptible to overcrowding.

Overcrowding in the frequency spectrum may cause interference of wireless communications, which can be particularly dangerous in critical care situations. In contrast, transmitter 22, in some embodiments, is capable of communicating data signals 24 in the bandwidth range of the Wireless Medical Telemetry Service (WMTS) band. WMTS is divided into three frequency blocks: (1) the 608-614 MHz frequency band; (2) the 1395-1400 MHz frequency band; and (3) the 1429-1432 MHz frequency band. Using the WMTS communication band advantageously enables system 10 to avoid overcrowding and interference.

In this example, system 10 includes a communications link 40 operable to facilitate the communication of data signals 24 to and/or from transmitter 22. Although communication link 40 comprises a single communication link in this example, any other number of communication links may be used without departing from the scope of the present disclosure. Communications link 40 may include any hardware, software, firmware, or combination thereof. In various embodiments, communications link 40 may comprise a communications medium capable of assisting in the communication of analog and/or digital signals. Communications link 40 may, for example, comprise a twisted-pair copper telephone line, a fiber optic line, a Digital Subscriber Line (DSL), a wireless link, a USB bus, a PCI bus, an ethernet interface, or a combination of these or other elements.

In this particular embodiment, at least a portion of communication link 40 comprises a wireless connection. In other embodiments, communication link 40 may be coupled to a communication network. For example, communication link 40 may be coupled to a data network, a public switched telephone network (PSTN), an integrated services digital network (ISDN), a local area network (LAN), a wide area network (WAN), a metropolitan area network (MAN), all or a portion of the global computer network known as the Internet, and/or other communication systems or combination of communication systems at one or more locations.

Receiver 26 operates to receive data signals 24 from transmitter 22. Although receiver 26 comprises a single receiver in this example, any other number of receivers may be used without departing from the scope of the present disclosure. Receiver 26 may be located in a patient's hospital room, in a patient's home, in CIF 30, or in any other suitable location to facilitate the communication of data signals 24 to and/or from transmitter 22. In some embodiments, one or more antennas 25 may be coupled to or contained within receiver 26. Antenna 25 may comprise any device capable of communicating data signals 24 between transmitter 22 and receiver 26.

Receiver 26 may comprise any device capable of receiving data signals 24 from one or more transmitters 22. In some embodiments, receiver 26 may comprise a transceiver capable of communicating and receiving signals to and/or from transmitter 22 or any other communication device. In other embodiments, receiver 26 may be capable of communicating and receiving signals to and/or from an intermediate booster or amplifier coupled to transmitter 22. In various embodiments, receiver 26 may be capable of scanning for new transmitters 22, so that when new transmitters 22 are coupled to system 10, system 10 may automatically recognize the new data signals associated with the new transmitters.

Conventional wireless communications systems may be susceptible to interference from other common devices such as cordless phones, pagers, or microwave ovens. Due to these various interference sources, it may also be desirable, in some cases, to use higher reliability transmission protocols. In certain embodiments, receiver 26 may be capable of waiting to receive two data signals 24 from transmitter 22 and comparing the two signals for fidelity. Alternatively, system 10 may implement two-way communications between transmitter 22 and receiver 26 to enable the use of acknowledgement signals, such as that used in association with the IEEE 802.11 communication protocol. In other embodiments, system 10 may implement intelligent communications software that allows for data checking in the event of sudden data jumps in the data signal stream.

System 10 also includes CIF 30 coupled to receiver 26. Although CIF 30 comprises a single CIF in this example, any other number of CIFs may be used without departing from the scope of the present disclosure. In some cases, implementing more than one CIF 30 advantageously enables system 10 to be more fault tolerant.

In this example, CIF 30 operates to process at least a portion of the unprocessed physiological data received from transmitter 22. CIF 30 may comprise any device capable of or having the functionality to process data signals 24 received from transmitter 22. For example, CIF 30 may comprise one or more computers that process data signals 24 received from various patients. In other embodiments, CIF 30 may process data signals 24 and store the processed data in a memory device coupled to CIF 30. In still another embodiment, CIF 30 may process data signals 24 and communicate the processed signals to a central monitoring station (CMS) 34 for storage and/or use by a care provider.

In this embodiment, CIF 30 couples to one or more medical diagnostic devices 32. Medical diagnostic devices 32 may comprise, for example, EKGs, heart monitors, or other medical devices depending upon the physiological parameters monitored. In some embodiments, devices 32 may be shared by a plurality of patients 20 coupled to CIF 30. In this particular embodiment, each device 32 couples to CIF 30. In other embodiments, one or more devices 32 may couple to one or more receivers 26 or to one or more CIFs 30.

In some embodiments, diagnostic devices 32 may be capable of interrogating the physiological data as it is received by CIF 30 and to check for errors in the data. For example, if an error is found, devices 32 may send a signal to transmitter 22 to resend the data. In addition, devices 32 may be designed to monitor the physiological data and look for extraordinary readings. In such a case, devices 32 may cause CIF 30 to alert a care provider that something is wrong with patient 20.

In a particular embodiment, system 10 may be configured such that an unexpected break in communications between patient 10 and CIF 30 triggers an alarm to warn a care provider of a potential system fault. For example, transmitter 22 may include an alert function capable of notifying a care provider of a failure of a component within system 10. In the event that transmitter 22 issues such an alert, system 10 may automatically, or a care provider may manually, couple transmitter 22 to a bed-side data station (BDS) so that no physiological data is lost. A BDS may comprise a data station located near a patient, such as within the same room as the patient. For example, the BDS may be located anywhere in a patient's hospital room, bedroom, or any other room where the patient is located. BDSs are discussed in more detail with respect to FIGS. 4 and 5. Once the problem within system 10 has been resolved, transmitter 22 may reestablish communication with CIF 30. Additionally, the BDS may transmit the physiological data received from transmitter 22 to CIF 30 for analysis and to ensure that no loss of patient data occurs. In some embodiments, transmitter 22 may include a memory device capable of storing the physiological data received from sensor 18 in the event of a failure within system 10. System 10 may also include back-up communications channels which may be utilized in the event of a failure of communication link 40, which can be particularly advantageous when monitoring patients in critical care environments.

Conventional patient data collection systems typically require a patient to be directly connected to diagnostic devices using an "umbilical cord" of wires. In most cases, the conventional system requires a separate set of diagnostic devices for each patient. In contrast, system 10 allows substantially unprocessed data to be wirelessly transmitted from patient 20 to CIF 30. The appropriate diagnostic devices 32 and/or CIF 30 then processes the unprocessed physiological data from patient 20. Moreover, system 10 may be implemented in a manner that enables numerous patients 20 to communicate data to CIF 30 and to share diagnostics devices 32. In some cases, implementing system 10 advantageously provides a cost savings over conventional patient data collection systems.

In other embodiments, system 10 may implement communications protocols and equipment technologies common to cordless phones, cellular phones, Internet, telephony, or any combination of these or other communications technologies. For example, system 10 may implement Code Division Multiple Access (CDMA), Time Division Multiple Access (TDMA), Wavelength Division Multiplexing (WDM), Frequency Division Multiplexing (FDM), packet addressing, frequency hopping, spread spectrum, IEEE 802.11 and 802.11b, and/or WiFi communication technologies. As another example, system 10 may implement line-of-sight (LOS) or near line-of-sight (NLOS) communications technologies using frequency ranges such as a 900 MHz band, a 2.4 GHz band, or a 5.8 GHz band. As used throughout this document the phrase "900 MHz band" refers to frequencies in the range of 800 MHZ to 1000 MHz. As used throughout this document the phrase "2.4 GHz band" refers to frequencies in the range of 1.5 GHz to 3.5 GHz. As used throughout this document the phrase "5.8 GHz band" refers to frequencies in the range of 4.5 GHz to 6.5 GHz. In some cases, implementing one or more of these communication technologies and frequency ranges may advantageously lead to a reduction of the cost of system 10.

System 10 is capable of being implemented in a clinical or hospital setting, in a patient's home, or in any other environment where a wireless medical communication system may be desired. In some embodiments, such as for use in a patient's home, transmitter 22 may communicate unprocessed physiological data associated with patient 20 to one or more BDSs located in the patient's home. The unprocessed physiological data may then be communicated via the Internet to CIF 30 for processing. CIF 30 may then communicate the processed physiological data and/or care giver instructions back to the BDS at the patient's home. For example, if CIF 30 determines that a patient's blood pressure is too low, CIF 30 may communicate signals to the BDS to trigger an alarm to alert a care giver of the situation. In addition, CIF 30 may communicate signals associated with a medical care instruction to be displayed on a screen associated with the BDS, such that a care giver or patient may receive that instruction.

Figure 2:
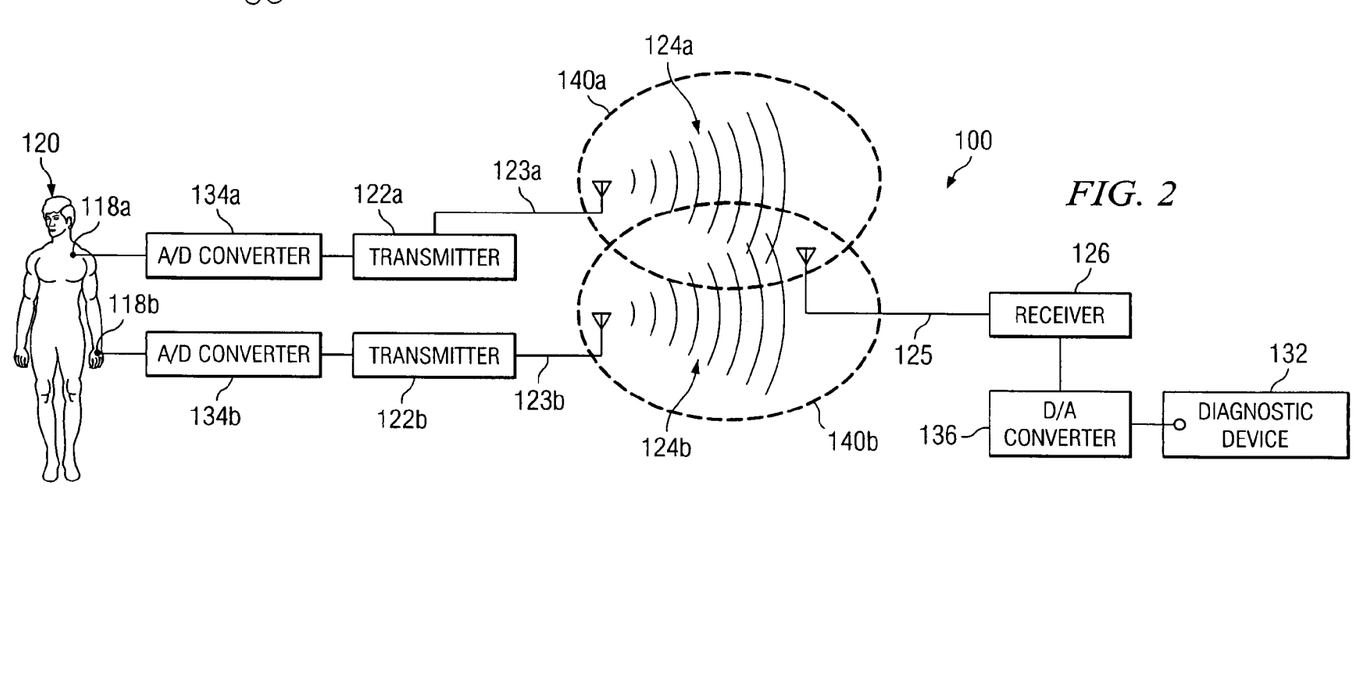
FIG. 2 is a block diagram of another embodiment of a medical communication system for communicating physiological parameters of a patient over one or more communication links.

FIG. 2 is a block diagram of a medical communication system 100 for communicating physiological parameters of a patient 120 over communication link 140a or 140b. In this example, system 100 includes sensors 118a and 118b, transmitters 122a and 122b, a receiver 126, and medical diagnostic device 132. The structure and function of sensors 118a and 118b, transmitters 122a and 122b, and communication links 140a and 140b can be substantially similar to sensor 18, transmitter 22, and communication link 40, respectively, of FIG. 1.

System 100 also includes one or more analog to digital converters (ADCs) 134 and at least one digital to analog converter (DAC) 136. In this example, ADC 134a and ADC 134b are coupled to transmitters 122a and 122b, respectively, and are capable of converting the monitored physiological parameter into a digital signal that transmitter 122 communicates to receiver 126. Receiver 126 is coupled to a DAC 136 operable to convert the received data signals 124 from a digital signal to an analog signal for use by one or more diagnostic devices 132 capable of interpreting analog signals.

In some embodiments, transmitter 122 may implement a communication protocol and/or communication technology for communicating data signals 124a and 124b. In one example, transmitters 124a and 124b implement CDMA, which enables the physiological data output from each sensor 118 to be spectrally encoded and the associated receiver 126 has the key to match that code. In this case, sensor 118 spectrally codes each signal with a unique identifier that enables receiver 126 to distinguish between data signals 124a and 124b that represent different physiological data of patients 120 and associate data signals 124a and 124b with the correct medical device 132. For example, each sensor 118 may have a unique code, and each receiver 126 may be programmed to match the sensor code (often called orthogonal codes).

In another example, transmitters 124a and 124b implement TDMA. In that case, data signals 124 are transmitted in blocks of data in a time-interleaved arrangement in a cyclic sequence. Each sensor 118 may be read in a timed sequence using "bursting" at transmitter 122, receiver 126, or both. In other embodiments, each transmitter 122a may be capable of communicating a data signal 124a that comprises a destination address that is different than a data signal 124b communicated from transmitter 122b.

Figures 3A, 3B, 4:
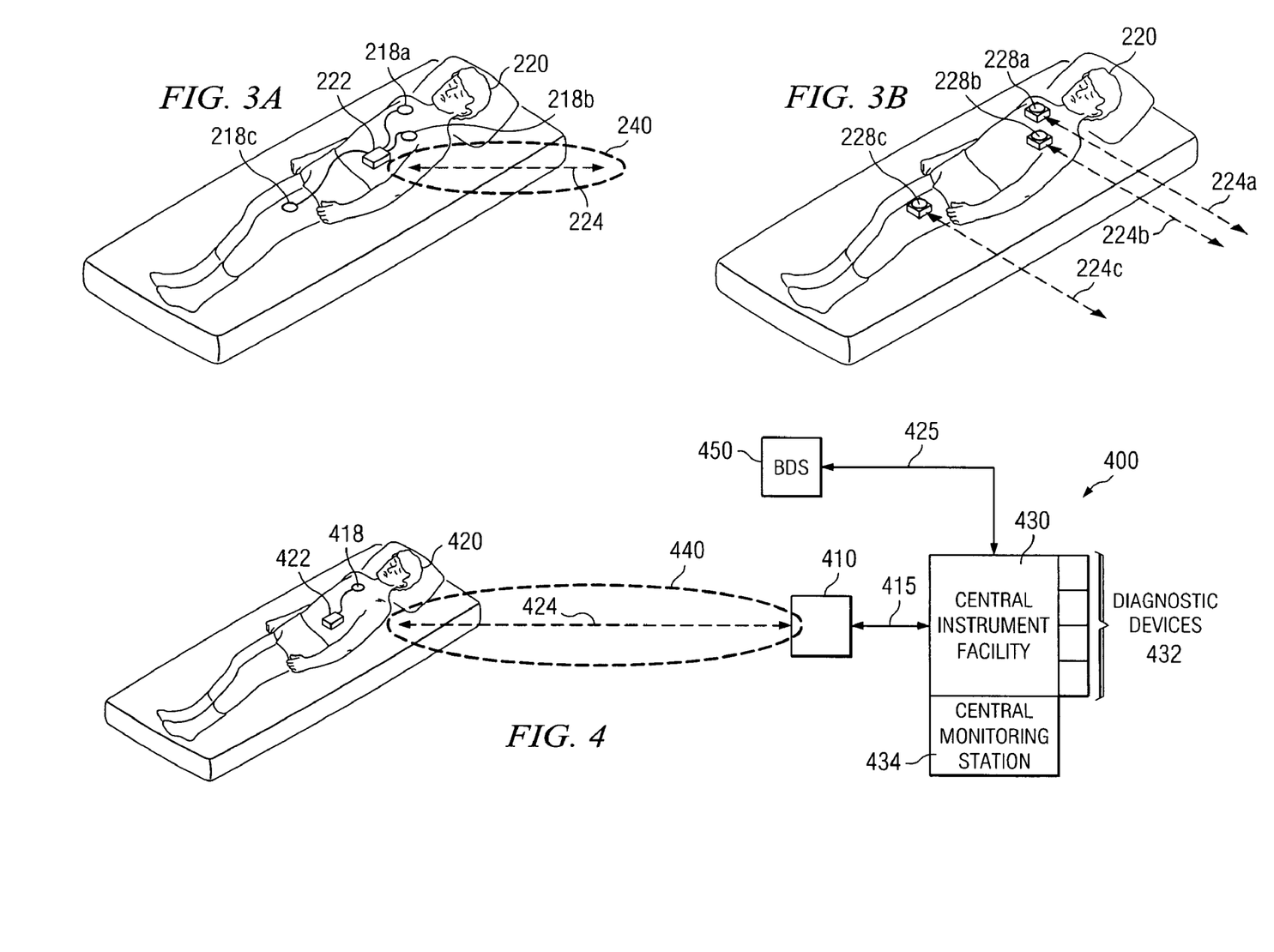
FIGS. 3A and 3B are block diagrams of sensor configurations.
FIG. 4 is a block diagram of one embodiment of a medical communication system for communicating physiological parameters of a patient.

FIG. 3A is a block diagram of an example sensor configuration. In this example, multiple sensors 218a through 218c are coupled to patient 220. The structure and function of sensors 218a through 218c can be substantially similar to sensor 18 of FIG. 1. Each sensor 218 is coupled to a single transmitter 222 capable of communicating the physiological data received from each sensor 218 over communication link 240. The structure and function of transmitter 222 and communication link 240 can be substantially similar to transmitter 22 and communication link 40 of FIG. 1. In this embodiment, transmitter 222 comprises a transceiver capable of communicating and receiving data signals 224 to and/or from patient 220.

FIG. 3B is a block diagram of another example sensor configuration. In this example, multiple sensor/transmitter units 228 are coupled to patient. Sensor/transmitter units 228 collect unprocessed physiological data from patient 220. Each sensor/transmitter unit 228 may separately and distinctly communicate the unprocessed physiological data associated with that unit 228 (e.g. 228a, 228b, and 228c) to an appropriate receiver, including but not limited to receiver 26 of FIG. 1 and/or receiver 126 of FIG. 2.

FIG. 4 is a block diagram of a medical communication system 400 for communicating physiological parameters of patient 420. In this example, system 400 includes a transmitter 422, a first communication link 440, a CIF 430, medical diagnostic devices 432, and CMS 434. In various embodiments, the structure and function of transmitter 422, first communication link 440, CIF 430, medical diagnostic devices 432, and CMS 434 can be substantially similar to the structure and function of transmitter 22, communication link 40, CIF 30, medical diagnostic devices 32, and CMS 34 of FIG. 1. System 400 also includes a repeater 410 coupled to transmitter 422 and a bed-side data station (BDS) 450 coupled to CIF 430.

In this example, transmitter 422 communicates data signals 424 at a low power over communication link 440 to repeater 410. In various examples, data signals 424 can be substantially similar to data signals 24 of FIG. 1. Repeater 410 operates to receive the low power data signals 424 and to amplify or boost the power level of data signals 424 for further communication over second communication link 415. Communicating data signals 424 from transmitters 422 at a relatively low power can, in some cases, operate to minimize damage to patient 420 that may result from high power transmissions.

In this example, CMS 434 operates to store and index the physiological data received from patient 420. In some embodiments, this enables a care provider, such as a doctor or a nurse, to oversee the status of a number of patients coupled to CIF 430. In addition, CIF 430, in this example, communicates the physiological data of patient 420 to BDS 450 over third communication link 425. BDS 450 may comprise any device or combination of devices capable of enabling a care provider local access to the physiological data collected by sensors 418.

In the illustrated embodiment, system 400 includes at least a first communications link 440, a second communications link 415, and a third communications link 425 each operable to facilitate the communication of data to and/or from CIF 430. Communications links 440, 415, and 425 may include any hardware, software, firmware, or combination thereof. In various embodiments, communications link 440, 415, and 425 may comprise any communications medium capable of assisting in the communication of analog and/or digital signals. Communications links 440, 415, and 425 may, for example, comprise a twisted-pair copper telephone line, a fiber optic line, a Digital Subscriber Line (DSL), a wireless link, a USB bus, a PCI bus, an ethernet interface, or any other suitable interface operable to assist in the communication of information to and/or from CIF 430.

Figure 5:
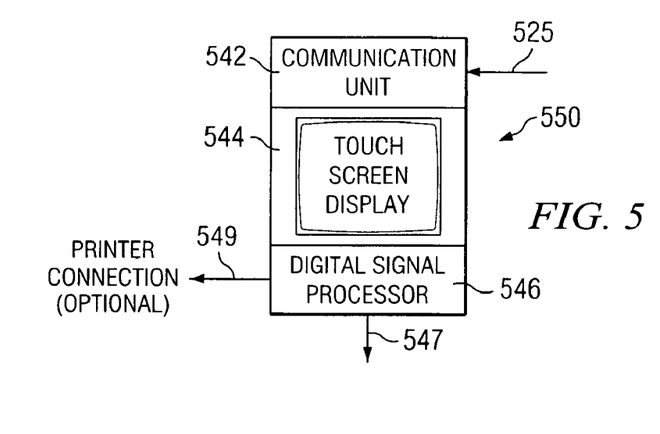
FIG. 5 is a block diagram of one embodiment of a bed-side data station.

FIG. 5 is a block diagram of one embodiment of a bed-side data station (BDS) 550. In this example, BDS 550 enables a care provider to have local access to a patient's physiological data at a remote location, such as in the patient's home or hospital room. In some cases, BDS 550 operates to receive historic and/or substantially real-time physiological data from a CIF coupled to BDS 550. In this example, BDS 550 includes a communications device 542 operable to receive physiological data communicated over communication link 525. Communications device 542 may comprise any device capable of receiving data signals communicated over communications link 525. In other embodiments, communications device 542 may comprise a transceiver capable of receiving and communicating data signals over communications link 525. In various embodiments, the structure and function of communication link 525 can be substantially similar to the structure and function of communication link 425 of FIG. 4.

BDS 550 also includes a touch-screen monitor 544 operable to display a patient's medical information and a digital signal processing (DSP) device 546 operable to store and/or analyze the patient's physiological data. Touch-screen 544 may comprise any device capable of displaying and/or inputting data relating to a patient. In other embodiments, touch-screen 544 may be capable of displaying a representation of multiple physiological data signals received over communications link 525. In various embodiments, DSP 546 is operable to perform statistical analysis of historical data and analyze the real-time data.

In some embodiments, BDS 550 is capable of receiving additional patient data from a care provider, drug administration data, schedules, reminders, and/or other related information using touch-screen monitor 544 or another input device. For example, authorized personnel may input the time and dosage of drugs administered to a patient. In this example, BDS 550 communicates this data over communication link 525 to a CIF for storage and analysis. In some embodiments, the CIF may periodically monitor the current and historical physiological data of a patient and alert the care provider of any abnormalities.

In this example, BDS 550 is capable of interfacing with a portable electronic data storage or analysis device, for example, a personal digital assistant (PDA) or a laptop computer, using communication link 547. BDS 550 may interface with these portable devices by implementing an appropriate communication protocol or technology, such as IMS, Bluetooth, or WiFi. In some cases, the communications protocol may prevent interference with the transmission of the unprocessed physiological data signal from a patient to a CIF over a communication link, such as communication link 40 of FIG. 1. In this example, BDS 550 also includes a printer connection 549 that can enable a care provider to print a hard copy of a patient's physiological data.

In some embodiments, access to BDS 550 may be secured such that only authorized personnel have access to a patient's physiological data. For example, a care provider may wear a badge that enables BDS 550 to wirelessly authenticate the care provider. In other embodiments, a care provider may use a unique pass-card that authenticates the care provider when the pass-card is swiped at BDS 550. In yet another embodiment, a care provider may use an infrared device that provides the care provider access to BDS 550 at the push of a button. Furthermore, authentication of the care provider may be granted by a voice recognition mechanism. Once authenticated, BDS 550 allows a care provider to access patient data stored and/or processed in a remote CIF. Although specific security technologies are described above, any appropriate security technology may be implemented without departing from the scope of the present disclosure.

Figure 6:
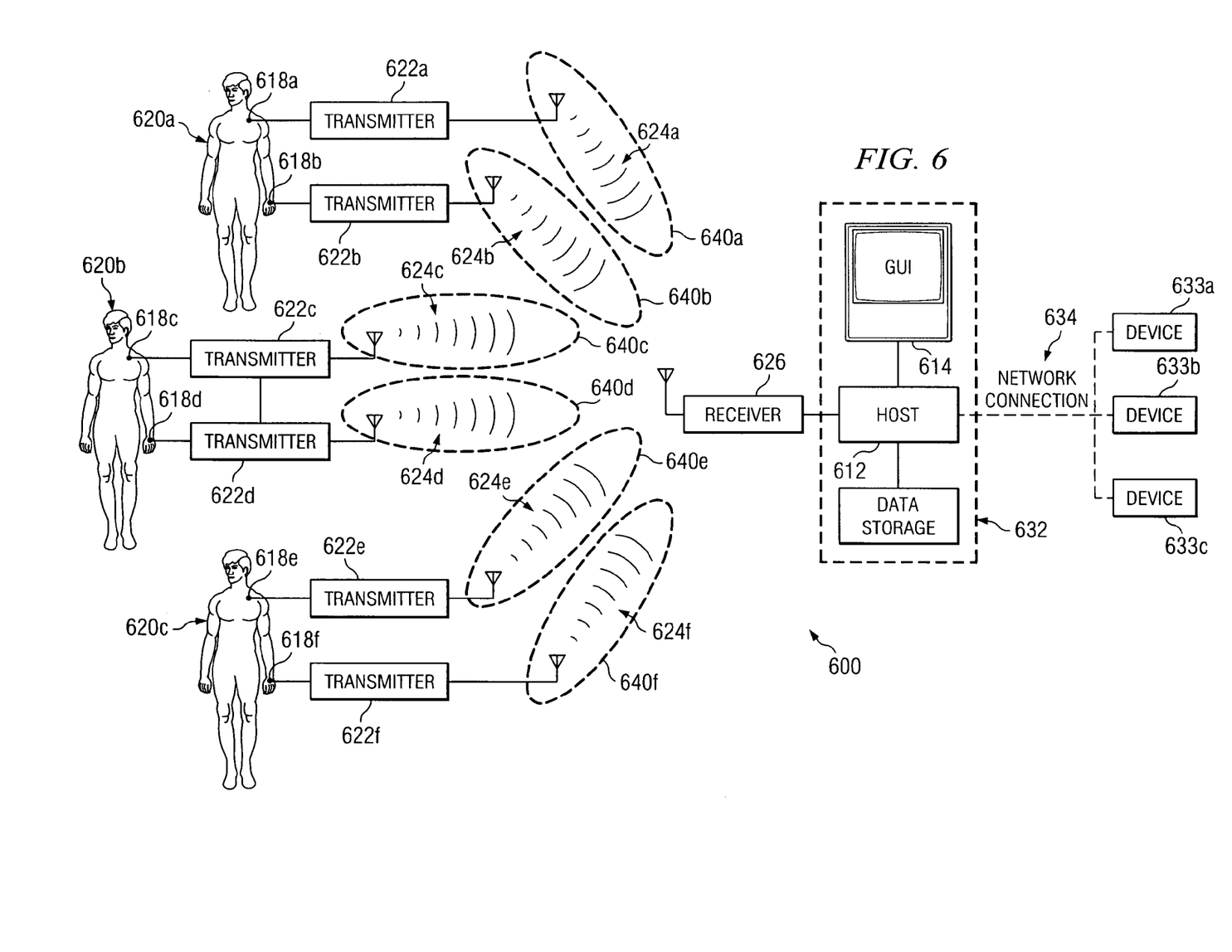
FIG. 6 is a block diagram of another embodiment of a medical communication system for communicating physiological parameters of a patient.

FIG. 6 is a block diagram of a medical communication system 600 for communicating physiological parameters of a patient 620. In this example, system 600 includes sensors 618a-618f, transmitters 622a-622f, communication links 640-640f, a receiver 626, and a medical diagnostic device 632. The structure and function of sensors 618, transmitters 622, communication links 640, receiver 626, and medical diagnostic device 632 can be substantially similar to sensors 18, transmitters 22, communication link 40, receiver 26, and medical diagnostic device 32 of FIG. 1. In this example, each data signal 624a-624f comprises the unprocessed physiological data and a patient/sensor identification code associated with each sensor 618a-618f.

In this example, at least one sensor coupled to each patient monitors the same physiological parameter monitored on at least one other patient. For example, sensors 618b, 618d, and 618f may monitor the blood pressure of patients 620a, 620b, and 620c, respectively, and sensors 618a, 618c, and 618e may monitor the heart rate of patients 620a, 620b, and 620c, respectively. In some cases, each sensor 618a-618f can sample the physiological parameter in a raster-scan pattern. In this example, each sensor 618a-618f is coupled to an associated transmitter 622a-622f. Each transmitter 622a-622f is capable of communicating its respective data signals 624a-624f over its respective communications link 640a-640f. In some cases, transmitters 622a-622f are capable of attaching a patient identification tag and a physiological parameter identification tag to each data signal 624a-624f.

Receiver 626 operates to receive data signals 624a-624f communicated from transmitters 622a-622f. Although receiver 626 comprises a single receiver in this example, any other number of receivers may be used without departing from the scope of the present disclosure. In this example, diagnostic device 632 is coupled to receiver 626 and is capable of performing a desired communicating and/or computing functionality. In some embodiments, diagnostic device 632 may be capable of processing, recording, and/or storing the physiological data for each of patients 620a-620c. In this particular embodiment, diagnostic device 632 is capable of processing and displaying the blood pressure associated with each of patients 620a-620c. Consequently, system 600 advantageously allows diagnostic device 632 to be shared between patients 620a-620c, which can reduce the required number of diagnostic devices.

In this example, diagnostic device 632 includes a host 612 capable of processing the unprocessed physiological data collected received by receiver 626. In operation, host 612 may execute with any of the well-known MS-DOS, PC-DOS, OS-2, MAC-OS, WINDOWS™, UNIX, or other appropriate operating systems. Host 612 may include a graphical user interface (GUI) 614 that enables a care provider to review, analyze, amend, and/or input data. Host 612 may comprise, for example, a desktop computer, a laptop computer, a server computer, a personal digital assistant, and/or any other computing or communicating device or combination of devices.

In this particular embodiment, diagnostic device 632 operates to process multiple substantially unprocessed physiological data signals 624 associated with multiple patients 620 coupled to medical device 632 in a loop format. The phrase "loop format" refers to a multiple time interval routine that allows a medical device to process a physiological parameter associated with one patient during each time interval. In some cases, diagnostic device 632 can randomly process data signals 624 associated with multiple patients 620. In other cases, diagnostic device 632 can sequential process data signals 624 associated with multiple patients 620. For example, during a first time interval, diagnostic device 632 can operate to process data signal 624b associated with patient 620a. In that example, during a second time interval, diagnostic device 632 can process data signal 624d associated with patient 620b and during a third time interval, diagnostic device 632 can process data signal 624f associated with patient 620c. Following the third interval, diagnostic device 632 can loop back and process data signals 624b associated with patient 620a. The time intervals during which diagnostic device 632 processes each of data signals 624 can comprise, for example, a fraction of a second or more. Processing data signals 624 in a loop format advantageously enables diagnostic device 632 to process data signals 624 associated with multiple patients, such that each of patients 620 "share" diagnostic device.

In this example, system 600 includes a plurality of secondary diagnostic devices 633a-633c coupled to diagnostic device 632 over network 634. The structure and function of secondary diagnostic devices 633a-633c can be substantially similar to diagnostic device 632 or diagnostic device 32 of FIG. 1. Secondary diagnostic devices 633a-633c are each capable of performing a desired communicating and/or computing functionality. In some embodiments, diagnostic device 633a-633c may be capable of processing, recording, and/or storing a desired physiological parameter associated with each of patients 620a-620c. In this particular embodiment, diagnostic device 633a is capable of processing and displaying the heart rate associated with each of patients 620a-620c.

Network 634 may comprise any wireless network, wireline network, or combination of wireless and wireline networks capable of supporting communication between network elements using ground-based and/or space-based components. For example, network 634 may comprise a data network, a public switched telephone network (PSTN), an integrated services digital network (ISDN), a local area network (LAN), a wide area network (WAN), a metropolitan area network (MAN), all or a portion of the global computer network known as the Internet, and/or other communication systems or combination of communication systems at one or more locations.

In some embodiments, one or more transmitters 622a-622f may implement a communication protocol and/or a communication technology for communicating data signals 624a-624f. For example, system 600 may implement CDMA and/or TDMA communication protocols. Implementing CDMA and/or TDMA communication protocols may enable receiver 626 to distinguish between data signals 624a-624f that represent different physiological parameters of patients 620a-620c. In addition, implementing a communication protocol, such as CDMA or TDMA, may enable receiver 626 to associate data signals 624a-624f with the correct diagnostic device.

In other embodiments, system 600 may implement a packet based communication network with data addressing that associates the physiological parameters with the proper patient 620a-620c. In a packet based communication network, each sensor 618a-618f has an associated network address contained in the header of the data packet communicated by the respective transmitter 622a-622f. In that case, receiver 626 is capable of processing the header to determine the network address for each sensor 618a-618f and ensure that the physiological parameter is communicated to the appropriate diagnostic device.

Figure 7:
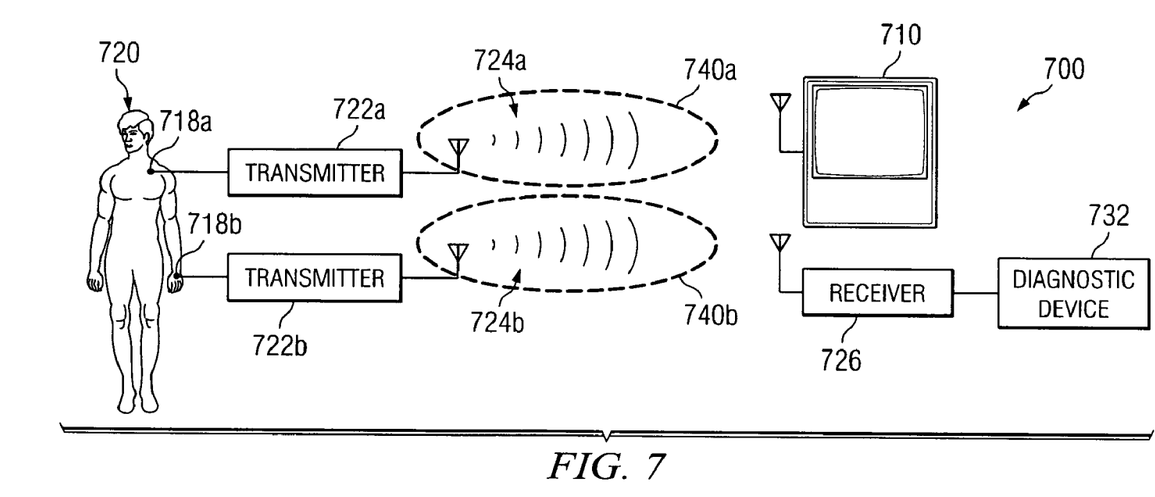
FIG. 7 is a block diagram of another embodiment of a medical communication system for communicating physiological parameters of a patient.

FIG. 7 is a block diagram of a medical communication system 700 for communicating physiological parameters of a patient 720. In this example, system 700 includes sensors 718a-718b, transmitters 722a-722b, communication links 740a-740b, a receiver 726, and a medical diagnostic device 732. The structure and function of sensors 718a-718b, transmitters 722a-722b, communication links 740a-740b, receiver 726, and medical diagnostic device 732 can be substantially similar to sensor 18, transmitter 22, communication link 40, receiver 26, and medical diagnostic device 32 of FIG. 1. System 700 also includes appliance 710 operable to receive data signals 724a-724b communicated by transmitters 722a-722b. In this embodiment, appliance 710 also operates to monitor the physiological parameters of associated with patient 720. Appliance 710 may comprise any device or combination of devices including one or more software and/or firmware modules operable to affect the function of the device. In some non-limiting examples, appliance 710 could comprise a computing and/or communicating device, such as, for example, a personal digital assistant (PDA), a cell phone, a digitized audio recorder/player, or any other digital or analog device.

Implementing a communication system that is similar to FIGS. 1, 2, 4, 6, or 7, can be particularly useful in a military environment. In military-type applications, sensors, such as sensor 18 of FIG. 1, may be capable of monitoring the physiological parameters of a soldier. In addition, the sensors may be capable of monitoring the presence of biological or chemical agents. The information collected by sensors 18 can be rapidly communicated to central locations, where medical personnel and military commanders can make time-critical decisions. Wireless medical communications systems, such those illustrated in FIGS. 1, 2, 4, 6, or 7, are particularly well suited to the military environment. In military applications it can be advantageous to use a "body-wide biosensor" network capable of individually monitoring battlefield personnel. In some cases, the medical communication systems illustrated in FIGS. 1, 2, 4, 6, or 7 can be implemented as a body-wide biosensor network.

A wireless medical communication system faces many operation constraints in military operations. Some of the military-specific constraints may include: (1) tighter security; (2) achieving minimum radio transmission and the risk of compromise; (3) extreme constraints on energy—need to last longer with minimum power; (4) self repair capabilities may need to be incorporated into the network; and (5) the need for physiological monitoring algorithms that are suited for these constraints.

For example, military applications may require lightweight equipment that require batteries or other energy sources that comprise minimal weight and/or a limited size. The limited size of the power source can equate to a limited amount of available energy. Therefore, a wireless medical communication device implemented in a military environment requires efficient energy usage. In addition, as the secrecy of troop movement is critical to battlefield survival, it is preferable to implement wireless medical communications systems that do not disclose the position of the troops. For example, if TDMA is implemented in a battlefield wireless medical communication system, troop location may be compromised by the regular transmission of data that occurs in TDMA.

In critical situations, accessibility to information by medical personnel can make a significant difference in soldier safety. Implementing a Query Need-to-Know Network (QNN) can advantageously provide a communication architecture well suited to implementation in the military environment. In a QNN, mobile nodes or a base station operate to query soldiers, based at least in part on the criticality of the combat situation, to request an update of the physiological data of the soldiers. For example, if soldiers are in a position of safety, then querying is relatively infrequent. On the other hand, if a group of soldiers are known to be in harms way, then their physiological data is queried more frequently since unnecessary transmission of information is greatly reduced, power consumption associated with the soldier's transmitter is correspondingly reduced. Furthermore, the less frequent the transmission of data, the more difficult it will be for the enemy to obtain troop locations based on the transmissions.

In QNN, the soldier first authenticates the query received from the mobile node or base station, and then communicates the information back to the querying station. In some embodiments, authenticating the query may include retrieving an authentication code from a look-up table and/or comparing a transmission frequency associated with the update request to a frequency stored in a memory device.

The QNN architecture provides a secure and low-power transmission in several ways. First, the soldier's transmitter/transceiver remains idle until queried, avoiding unnecessary exposure to enemy detection. Second, since the soldier can authenticate the request, queries from unknown sources can remain unanswered. Third, the transmission periodicity may be optimized based on global network information. Moreover, energy in transmission is often wasted due to contention or collisions of data (i.e., two soldiers transmit simultaneously, and then one or both need to retransmit after a random delay). Since the mobile node or base station controls the queries, contention may be avoided and repeat transmissions can be minimized.

A QNN is designed as a physical-layer aware architecture and protocol facilitating energy minimization and network simplicity. The path loss of radio transmission scales with distance in a greater-than linear fashion. Therefore, dividing a long distance transmission into several shorter distance transmissions can reduce communication energy. Implementation of a QNN advantageously reduces communication energy through the use mobile and/or intermediate nodes in the field. For example, a vehicle may serve as a base station. A QNN can also incorporate "smart sensor" technology into the network. Smart sensors are operable to process data thereby reducing the amount of data transmission. In addition QNN may incorporate "passive" sensors where the power for transmission may be extracted from the querying radio frequency (RF) beam.

In some embodiments, QNN can be implemented in a hospital setting. In those cases, one of the communication systems illustrated in FIGS. 1, 2, 4, 6, or 7, can continuously monitor patients and, at the same time, provide them with increased freedom of movement over current patient monitoring systems which use "umbilical cords" to directly connect the patient to diagnostic devices. To accomplish this, as discussed above, CIF 30 monitors patients and directs medical care if and when such a need is detected.

Figure 8:
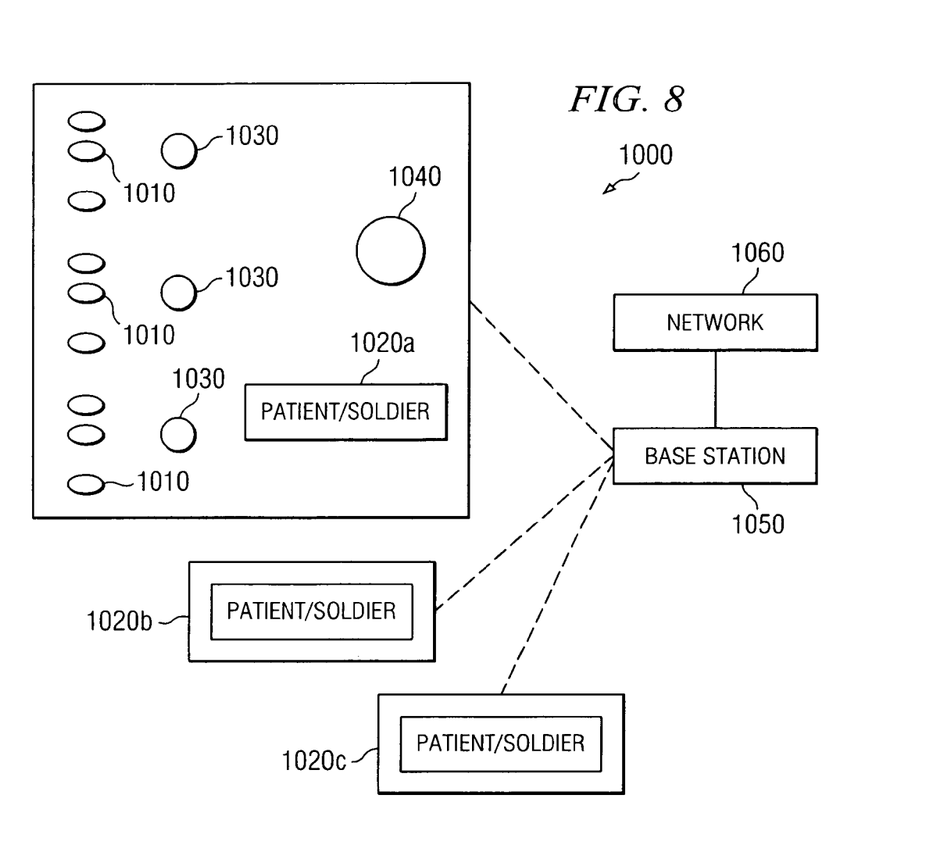
FIG. 8 is a block diagram of one embodiment of a network architecture for communicating physiological parameters of a patient.

FIG. 8 is a block diagram of one embodiment of a QNN architecture 1000 for communicating physiological parameters of a patient. QNN 1000 includes sensor/actuator nodes 1010, patient/soldiers 1020, mid-nodes 1030, master nodes 1040, and a base station 1050. In this example, sensors/actuators 1010 are implanted in or placed in close proximity to patient/soldier 1020. Sensor/actuator nodes 1010 on patient/soldier 1020 are relatively stationary whereas patient/soldier 1020 and base station 1050 move relative to each other.

In some embodiments, sensor/actuator nodes 1010 are controlled by mid-nodes 1030. In this example, mid-nodes 1030 are utilized because sensor/actuator nodes 1010 are designed to transmit at low signal strength. In certain embodiments, mid-nodes 1030 are operable to receive the command, communicate commands to sensors/actuator nodes 1010, and, in some cases, re-charge sensor/actuator nodes 1010. In the event of a system fault, mid-node 1030 is operable to take over control of another mid-node 1030. In some embodiments, mid-nodes 1030 may be added to and/or removed from QNN 1000 as needed.

In a particular embodiment, mid-nodes 1030 are controlled by master node 1040. Master node 1040 can be carried on person 1020 like a cell phone. Master node 1040 communicates with base station 1050. In some embodiments, master nodes 1040 can be added to and/or removed from QNN 1000 as needed.

Base station 1050 communicates with master nodes 1040 associated with other patients/soldiers 1020. In operation, base station 1050 may execute with any of the well-known MS-DOS, PC-DOS, OS-2, MAC-OS, WINDOWS™, UNIX, or other appropriate operating systems. Base station 1050 may comprise, for example, a desktop computer, a laptop computer, a server computer, a personal digital assistant, and/or any other computing or communicating device or combination of devices.

In certain embodiments, commands flow from base station 1050 to nodes 1030 and 1040 and data flows towards base station 1050 from nodes 1030 and 1040. In some embodiments, this general flow direction is alterable. For example, if an actuator of sensor/actuator node 1010 needs data from one or more sensors of sensor/actuator node 1010, commands may be routed directly between the sensor and the actuator rather than through base station 1050. In other embodiments, where global knowledge is distributed, data flows from base station 1050. For example, a chemical spill warning may trigger an adjustment in the physiological parameter-monitoring configuration. The complexity and reliability of QNN 1000 increases as patient/soldier 1020 moves toward base station 1050. Furthermore, computational power and transmitting power increase as patient/soldier 1020 moves closer to base station 1050.

In certain embodiments, base station 1050 is coupled to network 1060 to facilitate communication of patient data across a broader area. Network 1060 may comprise any wireless network, wireline network, or combination of wireless and wireline networks capable of supporting communication between network elements using ground-based and/or space-based components. For example, network 1060 may comprise a data network, a public switched telephone network (PSTN), an integrated services digital network (ISDN), a local area network (LAN), a wide area network (WAN), a metropolitan area network (MAN), all or a portion of the global computer network known as the Internet, and/or other communication systems or combination of communication systems at one or more locations.

Figure 9:
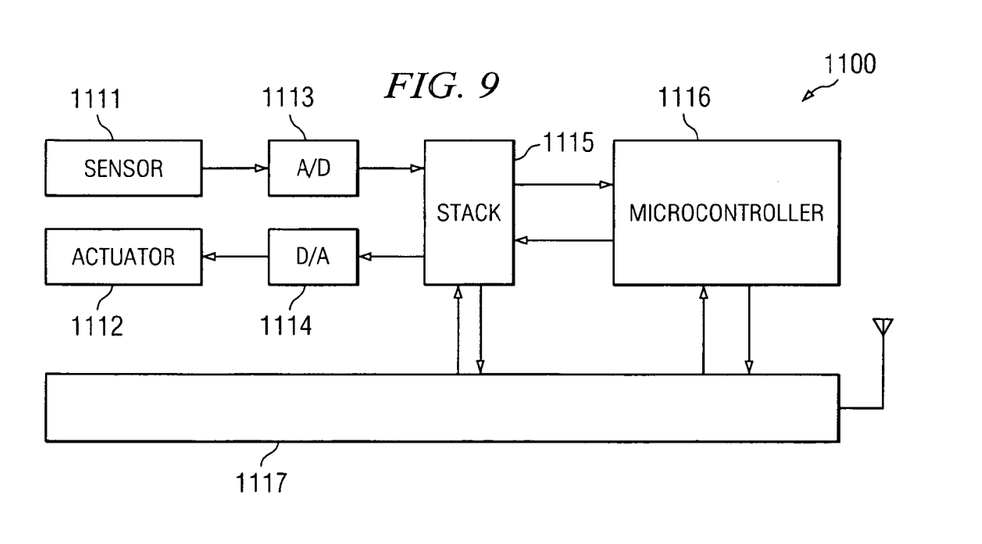
FIG. 9 is a block diagram of one embodiment of a sensor/actuator node.

FIG. 9 is a block diagram of one embodiment of a sensor/actuator node 1100. The structure and function of sensor/actuator node 1100 can be substantially similar to the structure and function of sensor/actuator node 1010 of FIG. 8. In some embodiments sensor/actuator node 1100 can communicate data up to 3-4 feet at a transmission rate of up to 10 Kbits/sec. In this example, sensor/actuator nodes 1100 includes a sensor 1111, an actuator 1112, an analog-to-digital converter (ADC) 1113 associated with sensor 1111, a digital-to-analog converter (DAC) 1114 associated with actuator 1112, a stack 1115 coupled to a micro-controller 1116, and circuitry for a transceiver, energy harvesting, and voltage and power supply scaling 1117.

In certain embodiments, the energy efficiency of sensor/actuator node 1100 is maximized by only allowing it to control the actuator, rather than performing a substantial amount of computations which require substantial energy usage. In other embodiments, computational power is used to compress data before communicating the data to mid-node 1030. Sensor data is stored in stack 1115 and controller 1116 performs operations on the data using a small scratch memory contained within controller 1116. Controller 1116 can control sensor parameters such as repetition rate, scan format, re-status, or a combination of these or other parameters. In some embodiments, the data received at sensor/actuator nodes 1110 is either physiological data and/or a command. Sensor data can be communicated by a radio interfacing with the stack. Command data received from mid-nodes 1030 is converted to analog form using DAC 1114. The analog signals are then used to control actuators 1112.

Figure 10:
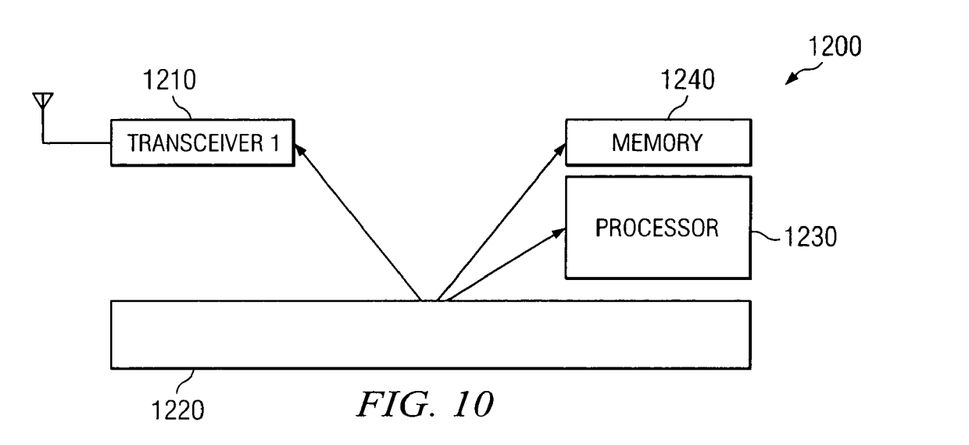
FIG. 10 is a block diagram of one embodiment of a mid-node.

FIG. 10 is a block diagram of one embodiment of a mid-node 1200. The structure and function of mid-node 1200 can be substantially similar to the structure and function of mid-node 1030 of FIG. 8. In this example, mid-node 1200 includes a transceiver 1210. Transceiver 1210 may comprise any device capable of communicating signals to and/or from other elements of a communication network. Mid-node 1200 also includes battery and voltage scaling devices 1220, a processor 1230, and a memory 1240. In some embodiments, mid-nodes 1200 are worn on a patient/soldier near a group of sensor/actuator nodes, such as sensor/actuator nodes 1010 of FIG. 8 or sensor/actuator nodes 1100 of FIG. 9. Processor 1230 is typically run at relatively lower clock speeds and controls both communications and computation. In certain embodiments, the radio range of mid-nodes 1200 can be approximately less than 3-4 feet. Communication data rates of mid-nodes 1200 can be approximately 50-100 Kbits/sec.

Figure 11:
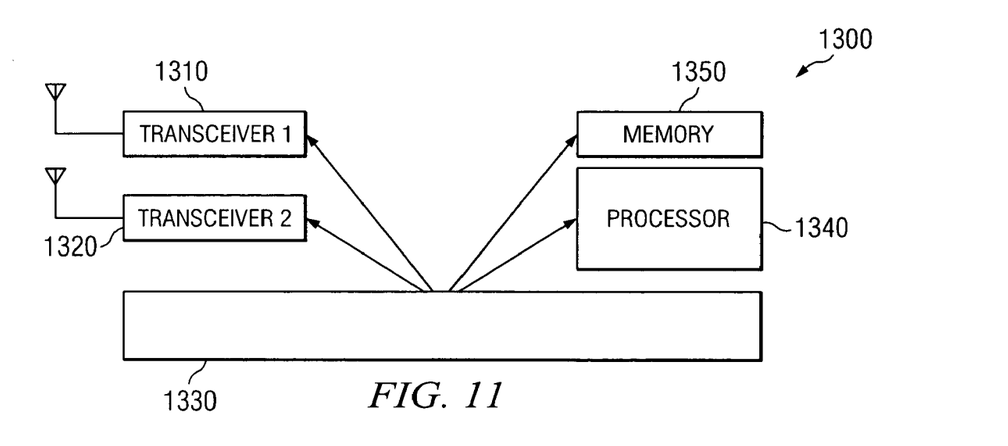
FIG. 11 is a block diagram of one embodiment of a master node.

FIG. 11 is a block diagram of one embodiment of a master node 1300. The structure and function of master node 1300 can be substantially similar to the structure and function of master node 1040 of FIG. 8. In this example, master node 1300 includes a transceiver 1310 capable of communicating data to and/or from sensor/actuator nodes 1010 of FIG. 8 and sensor/actuator node 1100 of FIG. 9. Master node 1300 also includes transceiver 1320 capable of communicating data to and/or from base station 1050 of FIG. 8. Transceiver 1310 and 1320 may comprise any devices capable of communicating signals to and/or from other elements of communication network.

In some embodiments, master node 1300 includes battery and voltage scaling devices 1330, a processor 1340, and a memory 1350. Master node 1300 can be worn on the clothing of patient/soldier 1020. In a particular embodiment, master node 1300 is lightweight, efficient, and minimally intrusive. The network of sensors and/or actuators is capable of communicating at a different frequency (using transceiver 1310) than the network in which master node 1300 communicates with a base station.

Although the present invention has been described with several embodiments, a multitude of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A communication system, comprising:
a plurality of transmitters adapted to be coupled to at least one patient at a first location, the plurality of transmitters communicating over a first communication link a plurality of data signals associated with the at least one patient, at least a portion of the first communication link comprising a wireless connection;
a first receiver coupled to the first communication link, the first receiver receiving at least a portion of the plurality of data signals communicated over the first communication link and communicating the portion of the plurality of data signals over a second communication link, wherein the first receiver communicates the portion of the plurality of data signals in a first data format over the second communication link, wherein the first data format comprises a time division multiple-access (TDMA) format and wherein at least a portion of the second communication link comprises an optical fiber;
at least one repeater coupled to the first receiver, the at least one repeater boosting a power level of the portion of the plurality of data signals for communication over the second communication link; and a central office station coupled to the at least one repeater, the central office station receiving the portion of the plurality of data signals communicated over the second communication link and communicating at least some of the portion of the plurality of data signals received by the central office station in a second data format over a third communication link to one or more receiving devices at a remote location, wherein the remote location is different than the first location and wherein the third communication link comprises a local access network coupled to the central office station at a proximal end of the local access network and coupled to the remote location at a distal end of the local access network; and one or more diagnostic devices coupled to the central office station, wherein the one or more diagnostic devices comprise a device selected from the group consisting of a heart monitor, an electrocardiogram, a blood pressure device, a temperature measuring device, a chemical composition device, and an electroencephalogram, wherein the second data format of at least a portion of the plurality of data signals communicated over the third communication link comprises a different format than the first data format communicated over the second communication link.

2. The system of claim 1, wherein the data signals comprise substantially unprocessed physiological data signals and a patient identifier.

3. The system of claim 1, wherein at least one of the plurality of transmitters communicates the data signals in the Wireless Medical Telemetry Service (WMTS) band.

4. The system of claim 1, wherein the second data format communicated over the third communication link is communicated over the third communication link is selected from the group consisting of Code Division Multiple Access (CDMA), wave division multiplexing (WDM), frequency division multiplexing (FDM), packet addressing, spread spectrum, frequency hopping, and Query-Need-To-Know (QNN).

5. The system of claim 1, further comprising:
a plurality of sensors coupled to the at least one patient, the plurality of sensors converting at least one physiological parameter associated with the at least one patient to an electronic format.

6. The system of claim 5, wherein at least some of the plurality of sensors coupling a patient identifier to the electronic format.

7. The system of claim 5, wherein the physiological parameter is selected from the group consisting of oxygen saturation in the blood (SpO2), blood pressure, blood sugar, body temperature, electrocardiogram (ECG), electroencephalogram (EEG), respiration rate, and heart rate.

8. The system of claim 1, wherein the central office station processing at least a portion of at least some of the data signals received from the second communication link.

9. The system of claim 8, wherein the central office station comprises a communication device communicating the processed data signals to a bed-side data station in a patient's room.

10. The system of claim 8, wherein the central office station further comprises at least one computational device monitoring the data signals and to store data in a memory device associated with the central office station.

11. The system of claim 1, wherein at least one of the data signals are communicated using a carrier frequency selected from the group consisting of a 900 MHz band, a 2.4 GHz band, and a 5.8 GHz band.

12. The system of claim 1, further comprising at least one back-up communication channel communicating at least one of the data signals to the at least one diagnostic device in the event that the first communication link fails.

13. The system of claim 1, wherein the third communication link is selected from the group consisting of a twisted-pair copper line, an optical fiber, a digital subscriber line, a wireless link, a USB bus, a PCI bus and an Ethernet interface.

14. The system of claim 1, wherein the remote location is selected from the group consisting of a patient's home and a hospital room.

15. The system of claim 1, wherein the at least one repeater is a signal amplifier.

16. The system of claim 1, wherein at least some of the plurality of data signals are in a packet format with an address and a payload, wherein the address associates each of the plurality data signals to the at least one patient.

17. The system of claim 1, wherein at least one of the plurality of transmitters communicates the data signals using a wireless technology selected from the group consisting of Internet, cellular, IEEE 802.11, IEEE 802.11b, or WiFi technologies.

18. A communication system capable of minimizing interference, comprising:
one or more sensors adapted to be coupled to at least one patient at a first location, the one or more sensors converting at least one physiological parameter associated with the at least one patient to a substantially unprocessed physiological data signal;

at least one transmitter coupled to the one or more sensors, the at least one transmitter communicating over a first communication link the substantially unprocessed physiological data signal, at least a portion of the first communication link comprising a wireless connection, wherein at least a portion of the wireless connection operates in a WMTS band;

at least one repeater coupled to the at least one transmitter, the repeater receiving at least a portion of the substantially unprocessed physiological data signal communicated over the first communication link, boosting a power level of the portion of the substantially unprocessed physiological data signal, communicating the portion of the substantially unprocessed physiological data signal in a first data format over a second communication link; and a central office station coupled to the at least one repeater, the central office station receiving the portion of the substantially unprocessed physiological data signal communicated over the second communication link and communicating at least some of the portion of the substantially unprocessed physiological data signal received by the central office station in a second data format over a third communication link to one or more receiving devices at a remote location, wherein the remote location is different than the first location and wherein the central office station is coupled to one or more diagnostic devices and wherein the third communication link comprises a local access network coupled to the central office station at a proximal end of the local access network and coupled to the remote location at a distal end of the local access network; and wherein the second data format of the portion of the data signal communicated over the third communication link comprises a different format than the first data format communicated over the second communication link.

19. The system of claim 18, further comprising one or more receivers coupled to the at least one transmitter, the one or more receivers receiving at least a portion of the substantially unprocessed physiological data signal.

20. The system of claim 18, wherein the at least one transmitter is adapted to be attached to the at least one patient.

21. The system of claim 18, wherein at least some of the one or more sensors attaching a patient identifier to the substantially unprocessed physiological data signal.

22. The system of claim 18, further comprising at least one medical diagnostic device coupled to a receiver, the at least one medical device processing the at least a portion of the substantially unprocessed physiological data signal.

23. The system of claim 22, wherein at least another patient is coupled to the at least one medical diagnostic device, the at least one medical diagnostic device receiving at least two substantially unprocessed physiological data signals communicated from that at least one transmitter, wherein each of the at least two substantially unprocessed physiological signals are associated with different patients.

24. The system of claim 22, wherein the at least one medical diagnostic device receiving and processing at least two substantially unprocessed physiological signals using a loop format.

25. The system of claim 22, wherein the at least one medical diagnostic device comprises a device selected from the group consisting of a heart monitor, an electrocardiogram, a blood pressure device, a temperature device, a chemical composition device, and an electroencephalogram.

26. The system of claim 22, further comprising at least one back-up communication channel communicating the substantially unprocessed physiological data signals to the at least one medical diagnostic device in the event that the communication link fails.

27. The system of claim 18, wherein the central office station communicating a data signal to a bed-side data station located in a patient room associated with the at least one patient.

28. The system of claim 18, wherein the central office station comprises at least one computational device monitoring the substantially unprocessed physiological data signals and to store the data in a memory device associated with the central office station.

29. The system of claim 18, wherein at least another portion of the wireless connection operates in a frequency band that is substantially different than the WMTS band.

30. The system of claim 29, wherein the frequency band that is substantially different than the WMTS band is selected from the group consisting of a 900 MHz band, a 2.4 GHz band, and a 5.8 GHz band.

31. The system of claim 18, wherein the substantially unprocessed physiological data signal comprises a patient identifier.

32. The system of claim 18, wherein the second data format communicated over the third communication link is communicated over the third communication link is selected from the group consisting of Code Division Multiple Access (CDMA), Time Division Multiple Access (TDMA), wave division multiplexing (WDM), frequency division multiplexing (FDM), packet addressing, spread spectrum, frequency hopping, and Query-Need-To-Know (QNN).

33. The system of claim 18, wherein the first data format communicated over the second data link is a time division multiple-access (TDMA) format.

34. The system of claim 18, wherein the second communication link is selected from the group consisting of a twisted-pair copper line, an optical fiber, a digital subscriber line, a wireless link, a USB bus, a PCI bus and an Ethernet interface.

35. The system of claim 18, wherein the third communication link is selected from the group consisting of a twisted-pair copper line, an optical fiber, a digital subscriber line, a wireless link, a USB bus, a PCI bus and an Ethernet interface.

36. The system of claim 18, wherein the remote location is selected from the group consisting of a patient's home and a hospital room.

37. The system of claim 18, wherein the at least one repeater is a signal amplifier.

38. The system of claim 18, wherein at least a portion of the substantially unprocessed physiological data signal is in a packet format with an address and a payload, wherein the address associates the data signals to the at least one patient.

39. The system of claim 18, wherein the at least one transmitter communicates the substantially unprocessed physiological data signal using a wireless technology selected from the group consisting of Internet, cellular, IEEE 802.11, IEEE 802.11b, or WiFi technologies.

40. The system of claim 18, wherein at least a portion of the second communication link comprises an optical fiber.

41. A wireless medical communication system, comprising:
   at least one transmitter adapted to be coupled to at least one patient at a first location, the at least one transmitter communicating over a first communication link a substantially unprocessed physiological data signal associated with the at least one patient, wherein at least a portion of the first communication link comprises a wireless connection;
   a first receiver coupled to the first communication link, the first receiver receiving at least a portion of the substantially unprocessed physiological data signal communicated over the first communication link and communicating the portion of the substantially unprocessed physiological data signal in a first data format over a second communication link, wherein at least a portion of the second communication link comprises an optical fiber; and
   a central office station coupled to the first receiver, the central office station receiving the portion of the substantially unprocessed physiological data signal communicated over the second communication link, to process at least a portion of the substantially unprocessed physiological data signal, and to communicate at least a portion of processed physiological data signal in a second data format over a third communication link to one or more receiving devices at a remote location, wherein the remote location is different than the first location, wherein at least a part of the substantially unprocessed physiological data signal received by the central office comprises a packet format having an address and a payload, wherein the address associates the data signal to the at least one patient and wherein the third communication link comprises a local access network coupled to the central office station at a proximal end of the local access network and coupled to the remote location at a distal end of the local access network; and
   wherein the second data format of the portion of the data signal communicated over the third communication link comprises a different format than the first data format communicated over the second communication link.

42. The system of claim 41, wherein at least a portion of the wireless connection operates in a Wireless Medical Telemetry Service (WMTS) band.

43. The system of claim 41, wherein the second data format communicated over the third communication link is communicated over the third communication link is selected from the group consisting of Code Division Multiple Access (CDMA), Time Division Multiple Access (TDMA), wave division multiplexing (WDM), frequency division multiplexing (FDM), packet addressing, spread spectrum, frequency hopping, and Query-Need-To-Know (QNN).

44. The system of claim 41, wherein the third communication links are selected from the group consisting of a twisted-pair copper line, an optical fiber, a digital subscriber line, a wireless link, a USB bus, a PCI bus and an Ethernet interface.

45. The system of claim 41, wherein the remote location is selected from the group consisting of a patient's home and a hospital room.

46. The system of claim 41, wherein the at least one repeater is a signal amplifier.

47. The system of claim 41, further comprising at least one repeater coupled to the at least one receiver, the at least one repeater boosting a power level of the portion of the substantially unprocessed physiological data signal as the portion of the substantially unprocessed physiological data signal is communicated over the second communication link.

48. The system of claim 41, wherein the first data format communicated over the second communication link is a time division multiple access (TDMA) format.

49. A communication system, comprising:
a plurality of transmitters, each of the plurality of transmitters adapted to be coupled to at least one patient at a first location, the plurality of transmitters communicating over a first communication link a data signal associated with at least one patient, at least a portion of the first communication link comprising a wireless connection;
a first receiver coupled to the first communication link, the first receiver receiving at least a portion of the data signal and to communicate the portion of the data signal in a first data format over a second communication link;
at least one repeater coupled to the receiver, the at least one repeater boosting a power level of the portion of the data signal for communication over the second communication link; and
a central office station coupled to the at least one repeater, the central office station receiving the portion of the data signal and to communicate at least some of the portion of the data signal in a second data format over a third communication link to a plurality of receiving devices at one or more remote locations, wherein the remote location is different than the first location and wherein the central office station is coupled to one or more data storage devices and one or more display units and wherein the third communication link comprises an optical fiber distribution network that operates to distribute the portion of the data signal to the plurality of receiving devices; and
one or more diagnostic devices coupled to the central office station, wherein the one or more diagnostic devices comprise a device selected from the group consisting of a heart monitor, an electrocardiogram, a blood pressure device, a temperature measuring device, a chemical composition device, and an electroencephalogram, wherein the second data format of the portion of the data signal communicated over the third communication link comprises a different format than the first data format communicated over the second communication link.

50. The system of claim 49, wherein the second data format communicated over the third communication link is communicated over the third communication link is selected from the group consisting of Code Division Multiple Access (CDMA), Time Division Multiple Access (TDMA), wave division multiplexing (WDM), frequency division multiplexing (FDM), packet addressing, spread spectrum, frequency hopping, and Query-Need-To-Know (QNN).

51. The system of claim 49, wherein at least a portion of the wireless connection comprises communication frequency selected from the group consisting of the WMTS band, a 900 MHz band, a 2.4 GHz band, and a 5.8 GHz band.

52. The system of claim 49, wherein at least the second communication link is selected from the group consisting of a twisted-pair copper line, an optical fiber, a digital subscriber line, a wireless link, a USB bus, a PCI bus and an Ethernet interface.

53. The system of claim 49, wherein the third communication link comprises a data network, a public switched telephone network, an integrated services digital network, a metropolitan area network, or at least a portion of the Internet.

54. The system of claim 49, wherein the at least one repeater is a signal amplifier.

55. The system of claim 49, wherein at least some of the data signals are in a packet format with an address and a payload, wherein the address associates the data signals to the at least one patient.

56. The system of claim 49, wherein the second data format communicated over the second communication link is time-division multiple access (TDMA).

* * * * *